US00H002181H

(19) United States

(12) Statutory Invention Registration

Levinson et al.

(10) Reg. No.: US H2181 H

(43) Published: Feb. 6, 2007

(54) HUMAN TPA PRODUCTION USING VECTORS CODING FOR DHFR PROTEIN

(75) Inventors: Arthur D. Levinson, Hillsborough, CA (US); Diane Pennica, Burlingame, CA (US); William J. Kohr, San Mateo, CA (US); Gordon A. Vehar, San Carlos, CA (US); David V. Goeddel, Hillsborough, CA (US); Elizabeth M. Yelverton, Seattle, WA (US); Christian C. Simonsen, Saratoga, CA (US)

(73) Assignee: Genentech, Inc., San Francisco, CA (US)

(21) Appl. No.: 07/663,244

(22) Filed: Feb. 28, 1991

Related U.S. Application Data

(63) Continuation of application No. 07/499,201, filed on Mar. 22, 1990, now Pat. No. 5,011,795, which is a continuation of application No. 07/149,032, filed on Jan. 27, 1988, now abandoned, which is a continuation of application No. 06/459,153, filed on Jan. 19, 1983, now abandoned.

(51) Int. Cl.
*C12N 15/09* (2006.01)

(52) U.S. Cl. ..... 435/69.2

(58) Field of Classification Search ..... 435/69.1, 435/69.2, 70.1, 91, 172.1, 172.3, 252.3–252.35, 435/320.1, 212, 240.1, 240.2; 536/27; 935/11, 935/12, 14, 32, 70, 71

See application file for complete search history.

(56) References Cited

U.S. PATENT DOCUMENTS

| | | | | |
|---|---|---|---|---|
| 3,904,480 A | | 9/1975 | Hull | 435/217 |
| 4,317,882 A | | 3/1982 | Horiguchi | 435/212 |
| 4,853,330 A | * | 8/1989 | Goeddel et al. | 435/252.33 |

FOREIGN PATENT DOCUMENTS

| | | |
|---|---|---|
| EP | 0005644 | 11/1979 |
| EP | 0041766 | 12/1981 |

OTHER PUBLICATIONS

Astedt, et al. *Thrombosis Research 134,* 1031–1037 (1978).

Barlow, et al. *Thrombosis and Urokinase* (eds Paoletti, R., Sherry, S.) Academic Press, p. 75–80 (1977).

Barlow, et al. Cold Spring Harbor Conferences on Cell Proliferation, vol. 2 (eds. Reich, E., Rifkin, D.B. & Shaw, E.) Cold Spring Harbor Press, p. 325–331 (1975).

Barnett, et al. *Proc. Soc. Exp. Biol. Med. 102,* 308–311 (1959).

Bernik, et al. *J. Lab. Clin. Med. 70,* 650–661 (1967).

Bernik, et al. *J. Clin. Invest. 48,* 1740–1753 (1969).

Bollen, et al. *Biochem. Biophys. Res. Comm. 97,* 207–215 (1980).

Bykowska, et al. *Biochimica et Biophysica Acta 703,* 113–115 (1982).

Christman, et al. *Biochim. Biophys. Acta 340,* 339–347 (1974).

(Continued)

*Primary Examiner*—Michael J. Carone

(74) *Attorney, Agent, or Firm*—Burns, Doane, Swecker & Mathis, L.L.P.

(57) ABSTRACT

A method for producing tissue plasminogen activator (t-PA) in eukaryotic host cells is disclosed. Enhanced levels of t-PA production are obtained by co-amplification of the t-PA gene through treatment of cultures transformed with mutant or wild-type DHFR with methotrexate.

2 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OTHER PUBLICATIONS

Christman, et al. Cold Spring Harbor Conferences on Cell Proliferation, vol. 2 (eds. Reich, E., Rifkin, D.B. & Shaw, E.) Cold Spring Harbor Press, p. 827–839 (1975).
Christman, et al. *J. Exp. Med. 142,* 419–434 (1975).
Christman, et al. "Plasminogen Activators Chapt. 2" in: Proteinase in Mammalian Cells and Tissues (ed. A. J. Barrett) Elsevier, Amsterdam, pp. 91–149 (1977).
Collen, et al. *Thromb Haemostas 48,* 294–296 (1982).
Dano, et al. *Biochimica et Biophysica Acta,* 613, 542–555 (1980).
Dano, et al. Cold Spring Harbor Conferences on Cell Proliferation, vol. (eds. Reich, E., Rifkin, D.B. & Shaw, E.) Cold Spring Harbor Press, p. 357–365 (1975).
Dano, et al. *J. Exp. Med.* 147,745–757 (1978).
Dano, et al. *Biochim. Biophys. Acta 566,* 138–151 (1979).
Goldberg, et al. Cold Spring Harbor Conferences on Cell Proliferation, vol. 2 (eds. Reich, E., Rifkin, D.B. & Shaw, E.) Cold Spring Harbor Press, p. 857–868 (1975).
Goldfarb, et al. *Biochemistry 19,* 5463–5471 (1980).
Heusen, et al. *Analytical Biochemistry 102,* 196–202 (1980).
Hisazumi, et al. *Urol. Res. 5,* 133–139 (1977).
Hull, et al. *Thrombosis Research 10,* 669–677 (1977).
Kucheriapati, et al. *Cell 15,* 1331–1340 (1978).
Laug, et al. *J. Cell Biology 84,* 281–293 (1980).
Lewis, L.J. *Thrombos. Haemostas. 42,* 895–900 (1979).
Loskutoff, D.J. *J. Cell. Physiol. 96,* 361–370 (1978).
Montesano, et al. *J. Nat. Cancer Inst. 59,* 1651–1658 (1977).
Mott, et al. *Biochem. Biophy. Res. Comm. 70,* 1150–1156 (1976).
Murano, et al. "Abbokinase", Summary Basis for Approval, NDA #76–1021 (Dec. 15, 1977) pp. 1–8, 10, and 12–16.
Opdenakker, et al. *Eur. J. Biochem. 121,* 269–274 (1982).
Painter, et al. *Amer. J. Physiol. 202,* 1125–1130 (1962).
Quigley, et al. *J. Biol. Chem. 249,* 4306–4311 (1974).
Reich, E. Cold Spring Harbor Conferences on Cell Proliferation, vol. 2 (eds. Reich, E., Rifkin, D.B. & Shaw, E.) Cold Spring Harbor Press, p. 333–342 (1975).
Rifkin, D.B. *J. Cell. Physiol. 97,* 421–428 (1978).
Rifkin, et al. Cold Spring Harbor Conferences on Cell Proliferation, vol. 2 (eds. Reich, E., Rifkin, D.B. & Shaw, E.) Cold Spring Harbor Press, p. 841–847 (1975).
Rifkin, et al. *J. Exp. Med. 139,* 1317–1328 (1974).
Rijken, et al. *J. Biol. Chem. 256,* 7035–7041 (1981).
Rijken, et al. Fibrinolysis vol. V. (Eds Davidson, J.F., Nilsson, I,M., Astedt, B) p. 236–239 (1981) See for example p. 236.
Roblin, et al. *Biochem. Biophys. Res. Comm. 82,* 165–172 (1978).
Schultz, et al. *Expl. Cell. Res. 96,* 47–57 (1975).
Seifert, et al. *Proc. Natl. Acad. Sci. USA 75,* 6130–6133 (1978).
Topp, et al. *Virology 106,* 282–291 (1980).
Unkeless, et al. Cold Spring Harbor Conferences on Cell Proliferation, vol. 2 (eds. Reich, E., Rilkin, D.B. & Shaw, E.) Cold Spring Harbor Press, p. 495–514 (1975).
Unkeless, et al. *J. Biol. Chem. 249,* 4295–4305 (1974).
Vetterlein, et al. *J. Biol. Chem. 255,* 3665–3672 (1980).
Williams, et al. *In Vitro 14,* 824–836 (1978).
Wilson, et al. *Cancer Research 40,* 933–938 (1980).
Wilson, et al. *Int. J. Cancer 22,* 390–399 (1978).
Wu, et al. *Biochemistry 16,* 1908–1913 (1977).
Astrup, T. Cold Spring Harbor Conferences on Cell Proliferation, vol. 2 (eds. Reich, E., Rilkin, D.B. & Shaw, E.) Cold Spring Harbor Press, p. 343–355 (1975).
Fischer, A. *Nature 157,* 442 (1946).
Fischer, A. *Biol. Rev. 22,* 178–194 (1947).
Loskutoff, et al. *Proc. Nat. Acad. Sci. USA 74,* 3903–3907 (1977).
Mahdavi, et al. *Biochimica et Biophysica Acta,* 583, 167–178 (1979).
Nozawa, R.T. *J. Cell. Physiol. 90,* 351–360 (1976).
Ossowski, et al. *J. Exp. Med. 138,* 1056–1064 (1973).
Ossowski, et al. *J. Biol. Chem. 249,* 4312–4320 (1974).
Pollack, et al. *Proc. Natl. Acad. Sci, U.S.A. 71,* 4792–4796 (1974).
Pollack, Cold Spring Harbor Conferences on Cell Proliferation, vol. 2 (eds. Reich, E., Rifkin, D.B. & Shaw, E.) Cold Spring Harbor Press, p. 885–899 (1975).
Rifkin, et al. *J. Cell Biology 73,* 47–55 (1977).
Rohrlich, et al. Annual Reports in Medicinal Chemistry–14, Section V. Topics in Biology, 229–239 (1979).
Sisskin, et al. *Journal of Cellular Physiology 102,* 141–153 (1980).
Unkeless, et al. *J. Exp. Med. 137,* 85–111 (1973).
Wang, et al. *Cancer Research 40,* 288–292 (1980).
Weber, M.J. *Cell 5,* 253–261 (1975).
Weber, Cold Spring Harbor Conferences on Cell Proliferation, vol. 2 (eds. Reich, E., Rifkin, D.B. & Shaw, E.) Cold Spring Harbor Press, p. 915–930 (1975).

* cited by examiner

HUMAN TPA PRODUCTION USING VECTORS CODING FOR DHFR PROTEIN

This is a continuing application under 35 U.S.C. 120/121 of U.S. Ser. No. 07/499,201, filed 22 Mar. 1990, now U.S. Pat. No. 5,011,795, which is a continuing application of U.S. Ser. No. 07/149,032, filed 27 Jan. 1988 (now abandoned), which is a continuing application of U.S. Ser. No. 06/459,153, filed 19 Jan. 1983 (now abandoned). Reference is hereby made under 35 U.S.C. 120/121 to U.S. Ser. No. 06/374,860, filed 5 May 1982, U.S. Ser. No. 06/398,003, filed 14 Jul. 1982, and U.S. Ser. No. 06/483,052, filed 7 Apr. 1983.

BACKGROUND OF THE INVENTION

The invention herein relates to the production of human tissue plasminogen activator (tPA) in a transformant host cell culture. More specifically, the invention relates to vectors, cells, and methods of producing tPA in conjunction with expression of the sequences for coding for dihydrofolate reductase (DHFR) protein in such cells.

The production of tPA using recombinant techniques has been disclosed in U.S. application Ser. No. 398,003 filed Jul. 14, 1982 which is a continuation in part of U.S. Ser. No. 374,860 filed May 5, 1982; the contents of both applications are incorporated herein by reference. These applications describe the construction of plasmids containing the coding sequences for tPA, and describe the activity and utility of tPA so produced.

It has also been found, as set forth in applications U.S. Ser. No. 06/459,152, filed 19 Jan. 1983, now U.S. Pat. No. 4,713,339, and U.S. Ser. No. 06/459,151, filed 19 Jan. 1983, now abandoned, and incorporated herein by reference, that a DNA sequence encoding for a DHFR protein can be utilized as a marker for transfection of a sequence coding for a desired heterologous protein in suitable host cells. The DHFR sequence can also be used as a secondary sequence permitting control of the production of the desired protein. These applications disclose such a use, both of wild type DHFR, and of a mutant DHFR which is resistant to methotrexate.

A problem frequently encountered in the production of polypeptides in a foreign host is the necessity to have some mechanism to regulate, usually to enhance, the production of the desired protein. In the case of tPA, which forms the subject matter of this invention, a secondary coding sequence comprising DHFR which is affected by an externally controlled parameter, such as methotrexate, is utilized to permit control of expression by control of the methotrexate (MTX) concentration.

Methotrexate is a drug which is normally fatal to cells capable of its uptake. However, certain cells are able to grow in the presence of controlled levels of MTX. One of the several mechanisms whereby methotrexate resistance is effected is that whereby amplification of the gene coding for the DHFR coding sequence is stimulated (Schimke, Robert T. et al, *Science,* 202: 1051 (1978); Biedler, J. L. et al, *Cancer Res.* 32: 163 (19/2); Chang, S. E., et al, *Cell,* 7: 391 (1976)).

It has further been shown that amplification of the gene for DHFR may further cause amplification of associated sequences which code for other proteins. This appears to be the case when the associated protein is hepatitis B surface antigen (HBsAq) (Christman, J. et al, *Proc. Natl. Acad. Sci.,* 79: 1815 (1982)); the *E. coli* protein XGPRT (Ringold, Gordon, et al, *J. Molec. and Appl. Gen.,* 1: 165 (1981)); and an endogenous sequence from a DHFR/SV40 plasmid combination (Kaufman, R. F. et al, *J. Molec. Biol.,* 159: 601 (1982)).

Other mechanisms for conferring methotrexate resistance include diminution of the binding affinity of the DHFR protein, so that it is less susceptible to methotrexate (Flintoff, W. F. et al, *Somat. Cell Genet.,* 2: 245 (19/6)) but in this instance, amplification appears to occur as well.

Thus it would appear that the genes both for wild type DHFR and for DHFR which is resistant to MTX by virtue of its own decreased binding capacity are amplified by the presence of MTX. Hence, in principle, the invention herein concerns using the impact of DHFR sequence amplification on associated protein coding sequences to provide a control mechanism which permits enhanced expression levels of tPA sequences in the presence of MTX, or by virtue of prior treatment of transformed cells with MTX.

As described in U.S. Ser. No. 398,003, tPA is a fibrinolytic substance which can be recovered from human melanoma cells (EPO Patent Application Publn. No. 0041766). This product has been isolated and characterized [Weiman et al, *The Lancet,* II (8250): 1018 (1981)]. Its fibrinolytic activity is analogous to that of two commercially available proteins, streptokinase and urokinase, which are indicated for the treatment of acute cardiovascular diseases such as myocardial infarct, stroke, pulmonary embolism, deep vein thrombosis, peripheral arterial occlusion and other venous thromboses. The etiological basis for these diseases is apparently either a partial or total occlusion of a blood vessel by a blood clot. Thus traditional anticoagulant therapy for example, treatment with heparin or coumarin, is not effective as it will merely prevent the formation of further clots, but not result in the dissolution of clots already formed. The fibrinolytic agents, streptokinase, urokinase, and plasminogen activator all operate similarly. They convert the inactive precursor plasminogen into plasmin which is capable of dissolving the fibrin of which these clots are composed. Plasminogen activator has a high affinity for fibrin, and thus preferentially activates plasminogen associated with the fibrin desired to be dissolved. On the other hand, streptokinase and urokinase do not; hence, much of the plasmin formed is formed in circulating blood and is neutralized before it can reach the targeted clot. Furthermore, as these compounds create circulating rather than fibrin bound plasmin, other clotting factor proteins in circulation such as fibrinogen, Factor V, and Factor VIII are also attacked by the activated protein causing a hemorrhagic potential. Furthermore, streptokinase is strongly immunogenic.

Plasminogen activator overcomes the foregoing difficulties by specifically attacking plasminogen already bound to fibrin. The present invention concerns a method of increasing and controlling the production of this valuable protein in recombinant cultures by effecting control on amplification of the sequence for DHFR protein.

SUMMARY OF THE INVENTION

In one aspect, the invention herein concerns plasmids which contain coding sequences for human tissue plasminogen activator (tPA) and a DHFR protein, and which are effective in expressing both of them. In another aspect, the invention concerns cells transformed with these vectors.

In other aspects, the invention also concerns methods for producing tPA by taking advantage of the environmentally controlled response of DHFR coding sequences co-transfected with the tPA sequence, and the tPA so produced.

DETAILED DESCRIPTION

A. Definitions

Figure 1:
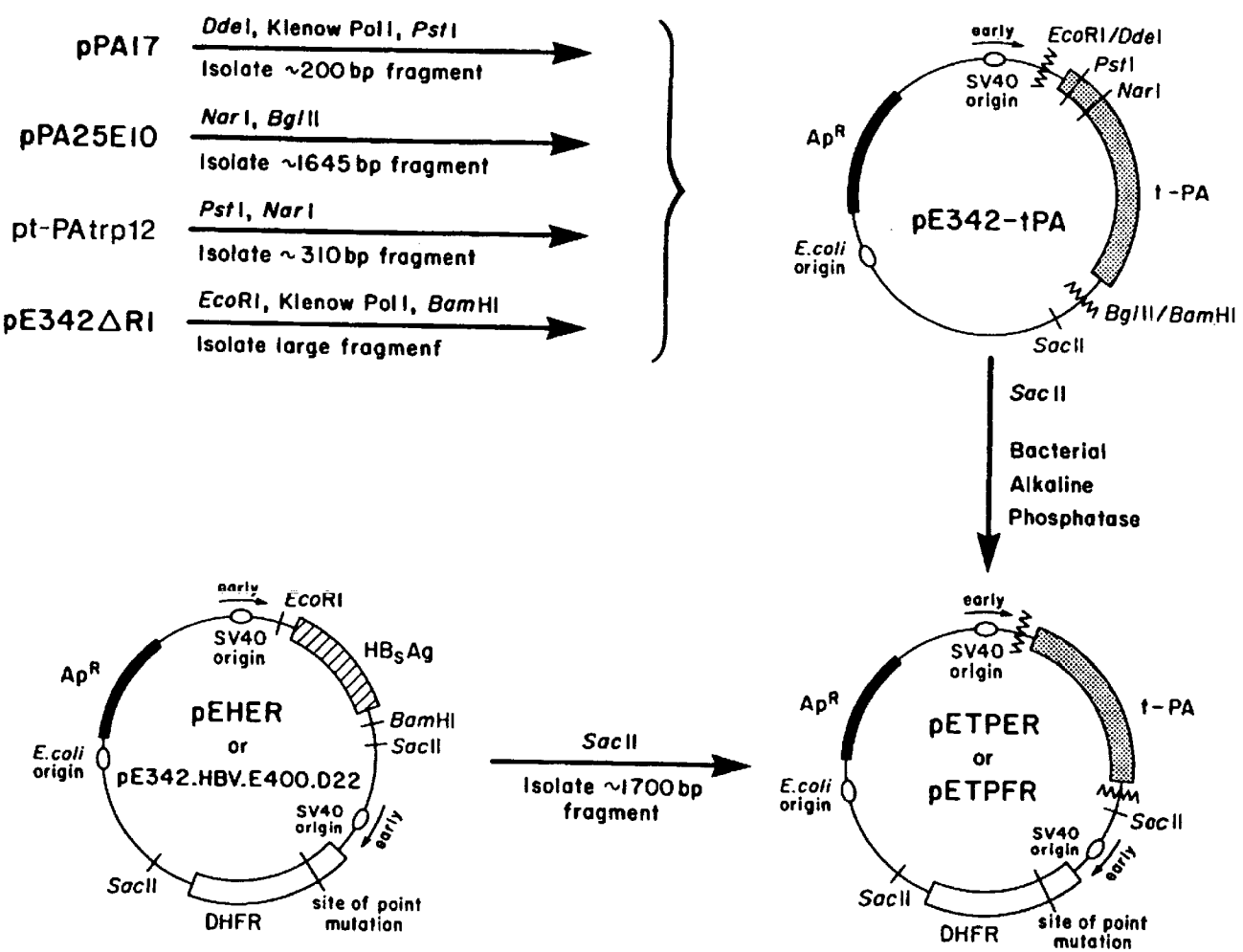
FIG. 1 is a schematic diagram of the construction of the exemplified DHFR (mutant or wild type)/tPA encoding plasmids.

As used herein:

Human "tissue plasminogen activator" (t-PA) is a fibrinolytic protein as described in U.S. Pat. No. 4,752,603, issued Jun. 21, 1988, which is a continuation of Ser. No. 640,550, filed Aug. 15, 1984, now abandoned, which is a continuation of Ser. No. 272,093, filed Jun. 10, 1981, which is a continuation-in-part of Ser. No. 183,638 filed Sep. 3, 1980. Said applications Ser. Nos. 272,093 and 183,638, incorporated herein by reference, describe cultivation and recovery of human t-PA in Example 1, first two paragraphs.

"DHFR protein" refers to a protein which is capable of the activity associated with dihydrofolate reductase (DHFR) and which, therefore, is required to be produced by cells which are capable of survival on medium deficient in hypoxanthine, glycine, and thymidine (–HGT medium). In general, cells lacking DHFR protein are incapable of growing on this medium, cells which contain DHFR protein are successful in doing so.

"Cells sensitive to MTX" refers to cells which are incapable of growing on media which contain the DHFR inhibitor methotrexate (MTX). Thus, "cells sensitive to MTX" are cells which, unless genetically altered or otherwise supplemented, will fail to grow under ambient and medium conditions suitable for the cell type when the MTX concentration is 0.2 μg/ml or more. Some cells, such as bacteria, fail to exhibit MTX sensitivity due to their failure to permit MTX inside their cell boundaries, even though they contain DHFR which would otherwise be sensitive to this drug. In general, cells which contain, as their DHFR protein, wild type DHFR will be sensitive to methotrexate if they are permeable or capable of uptake with respect to MTX.

"Wild type DHFR" refers to dihydrofolate reductase as is ordinarily found in the particular organism in question. Wild type DHFR is generally sensitive in vitro to low concentrations of methotrexate.

"DHFR protein with low binding affinity for MTX" has a functional definition. This is a DHFR protein which, when generated within cells, will permit the growth of MTX sensitive cells in a medium containing 0.2 μg/ml or more of MTX. It is recognized that Such a functional definition depends on the facility with which the organism produces the "DHFR protein with low binding affinity for MTX" as well as upon the protein itself. However, as used in the context of this invention, such a balance between these two mechanisms should not be troublesome. The invention operates with respect to conferring the capability of surviving these levels of MTX, and it is not consequential whether the ability to do so is impacted by increased expression in addition to the innate nature of the DHFR produced.

"Expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition. and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques. As defined herein, tPA produced in the amounts achieved by virtue of this transformation, rather than in such lesser amounts, or, more commonly, in such less than detectable amounts, as would be produced by the untransformed host.

B. Detailed Description

B.1 Most Cell Cultures and Vectors

The vectors and methods disclosed herein are suitable for use in host cells over a wide range of prokaryotic and eukaryotic organisms.

In general, or course, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 ATCC No. 31537). These examples are, of course, intended to be illustrative rather than limiting.

Prokaryotes may also be used for expression. The aforementioned strains, as well as *E. coli* W3110 ($F^-$, $\lambda^-$, prototrophic, ATTC No. 27325), bacilli such as *Bacillus subtilus,* and other enterobacteriaceae such as *Salmonella typhimurium* or *Serratia marcesans,* and various pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR 322, a plasmid derived from an *E. coli* species (Bolivar, et al., *Gene* 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, *Nature,* 275: 617 (1978); Itakura, et al, *Science,* 198: 1056 (1977)); (Goeddel, et al *Nature* 281: 544 (1979)) and a tryptophan (trp) promoter system (Goeddel, et al, *Nucleic Acids Res.,* 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, *Cell* 20: 269 (1980)).

In addition to prokaryotes, eukaryotic microbes, such as yeast cultures may also be used. *Saccharomyces cerevisiae,* or common baker's yeast is the most commonly used among eukaryotic microorganisms, although a number of other strains are commonly available. For expression in *Saccharomyces,* the plasmid YRp7, for example, (Stinchcomb, et al, *Nature,* 287: 39 (1979); Kingsman et al, *Gene,* 7: 141 (1979); Tschemper, et al, *Gene,* 10: 157 (1980)) is commonly used. This plasmid already contains the trp1 gene which provides a selection marker for a mutant strain of yeast lacking the ability to grow in tryptophan, for example ATCC No. 44076 or PEP4-1 (Jones, *Genetics,* 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.,* 255: 2073 (1980)) or other glycolytic enzymes (Hess, et al, *J. Adv. Enzyme Reg.,* 7: 149 )1968); Holland, et al, *Biochemistry,* 17: 4900 (1978)), such as enolse, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However interest has been greatest in vertebrate cells, and propagation of vertebrate cells in culture (tissue culture) has become a routine procedure in recent years [*Tissue Culture,* Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences. It will be understood that this invention, although described herein in terms of a preferred embodiment, should not be construed as limited to those sequences exemplified.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature,* 273: 113 (1978) incorporated herein by reference. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provide such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

B.2 Selection of Cell Lines

In selecting a preferred host cell for transfection by the vectors of the invention, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (USA) 77: 4216 (1980), incorporated herein by reference.

On the other hand, if DHFR protein with low biding affinity for MTX is used as the controlling sequence, it is not necessary to use DHFR resistant cells. Because the mutant DHFR is resistant to methotrexate, MTX containing media can be used as a means of selection provided that the host cells themselves are methotrexate sensitive. Most eukaryotic cells which are capable of absorbing MTX appear to be methotrexate sensitive. One such useful cell line is a CHO line, CHO-K1 ATCC No. CCL 61.

The example which is set forth hereinbelow describes use of CHO cells as host cells, and expression vectors which include the SV40 origin of replication as a promoter. However, it would be well within the skill of the art to use analogous techniques to construct expression vectors for expression of desired protein sequences in alternative eukaryotic host cell cultures.

B.3 Methods Employed

If cells without formidable cell wall barriers are used as host cells, transfection is carried out by the calcium phosphate precipitation method as described by Graham and Van der Eb, *Virology,* 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N. et al *Proc. Natl. Acad. Sci.* (USA), 69: 2110 (1972).

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.,* 8: 4057 (1980) incorporated herein by reference.

For ligation approximately equimolar amounts of the desired components, suitably end tailored to provide correct matching are treated with about 10 units T4 DNA ligase per 0.5 μg DNA. (When cleaved vectors are used as components, it may be useful to prevent religation of the cleaved vector by pretreatment with bacterial alkaline phosphatase.)

The ligation mixture was used to transform *E. coli* K12 strain 294 (ATCC 31466), and successful transformants were selected by ampicillin resistance. Plasmids from the transformants were prepared, analyzed by restriction and/or sequenced by the method of Messing, et al, *Nucleic Acids Res.,* 9:309 (1981) or by the method of Maxam, et al, *Methods in Enzymology,* 65:499 (1980).

Amplification of DHFR protein coding sequences is effected by growing host cell cultures in the presence of approximately 20–500,000 nM concentrations of methotrexate, a competitive inhibitor of DHFR activity. The effective range of concentration is highly dependent, of course, upon the nature of the DHFR gene, protein and the characteristics of the host. Clearly, generally defined upper and lower limits cannot be ascertained. Suitable concentrations of other folic acid analogs or other compounds which inhibit DHFR could also be used. MTX itself is, however, convenient, readily available and effective.

B.4 Results Obtainable

The methods of the invention permit the production in host cell cultures of antigenically active tPA protein in amounts greater than 0.1 pg per cell per day. With suitable application of amplifying conditions, amounts greater than 20 pg can be obtained. Stated in alternate terms, gene expression levels resulting in production of more than $9\times10^{-6}$ units, or, with suitable amplification, more than $18\times10^{-5}$ units of tPA activity are achieved.

C. Examples

The following examples are intended to illustrate but not to limit the invention. In the examples here, a CHO cell line suitable for the type of DHFR protein coding sequence to be introduced was employed as a host cell culture in each case. However, other eukaryotic and prokaryotic cells are suitable for the method of the invention as well.

C.1 Production of tPA Using DHFR Protein with a Low Binding Affinity for MTX

C.1.A Vector Construction

The sequence encoding human tissue plasminogen activator (tPA) is inserted, an expression plasmid for a mutant DHFR with low binding affinity for MTX, described in copending application U.S. Ser. No. 06/459,151, incorporated herein by reference, by the following procedure (see FIG. 1):

cDNA plasmids encoding tPA have been described by Goeddel et al, application Ser. No. 374,860, filed May 5, 1982, and Ser. No. 398,003, filed 14, Jul. 1982, which are hereby incorporated by reference.

Human melanoma cells (Bowes) (ATCC CRL 9607) were used. The melanoma cells were cultured to confluent monolayers in 100 ml Earles Minimal Essential Media supplemented with sodium bicarbonate (0.12 percent final concentration), 2 mM glutamine and 10 percent heat-inactivated fetal calf serum. To confirm that the melanoma cells were actively producing human plasminogen activator, human melanoma cells were cultured to confluency in a 24 well microliter dish. Either in the presence or absence of 0.33 μM in the protease inhibitor aprotinin, the cells were washed once with phosphate buffered saline and 0.3 ml of serum free methionine free medium was added. 75 μCi of [$^{35}$S]-methionine was added and the cells were labeled at 37° C. for 3 hours. At the end of the 3 hour labelling period the media was removed from the cells and treated with either plasminogen activator specific IgG or pre-immune sera for immunoprecipitation (Oppermann, et al., *Virology* 108, 47 (1981)). The immunoprecipitated products were displayed by electrophoresis on a 10 percent SDS-acrylamide gel. The slab gel was fixed, dried and subjected to fluorography.

Total RNA from melanoma cell cultures was extracted essentially as reported by Ward, et al., (*J. Virol.* 9, 61 (1972)). Cells were pelleted by centrifugation and then resuspended in 10 mM NaCl, 10 mM Tris-HCl pH 7.5, 1.5 mM $MgCl_2$. Cells were lysed by the addition of NP-40 (1 percent final concentration), and nuclei were pelleted by centrifugation. The supernatant contained the total RNZ which was further purified by multiple phenol and chloroform extractions. The aqueous phase was made 0.2 M in NaCl and then total RNA was precipitated by the addition of two volumes of ethanol. Oligo-dT cellulose chromatography was utilized to purify mRNA from the total RNA preparations. Typical yields from 10 grams of cultured melanoma cells were 5 to 10 milligrams of total RNA and 50–200 micrograms of Poly(A) plus mRNA.

Fractionation of PolyA$^+$ mRNA (200 (μg) (Aviv, et al., *Proc. Natl. Acad. Sci.* (*USA*) 69, 1408 (1927)) was performed by electrophoresis through urea-agarose gels. The slab agarose gel (Lehrach, et al., *Biochemistry* 16, 4743 (1977) and Lynch, et al. *Virology* 98, 251 (1979)) was composed of 1.75 percent agarose, 0.025 M sodium citrate, pH 3.8 and 6 M urea. Electrophoresis was performed for 7 hours at 25 milliamps and 4° C. The gel was then fractionated with a razor blade. The individual slices were melted at 70° C. and extracted twice with phenol and once with chloroform. Fractions were then ethanol precipitated and subsequently assayed by in vitro translation in a rabbit reticulocyte lysate system, Bethesda Research Lab. (Lodish, *Am. Rev. of Biochem.* 45, 40 (1976) and Pelham, et al., *Eur. J. Biochem.* 43, 247 (1976)), supplemented with dog pancreas microsomes as follows: Translations were performed using 25 μCi of [$^{35}$S]-methionine and 500 nanograms of each gel slice RNA in a final volume of 30 μl containing 25 mM HEPES, 48.3 mM potassium chloride, 10 mM creatine phosphate. 19 amino acids at 50 mM each, 1.1 mM magnesium chloride 16.6 mM EDTA, 0.16 mM dithiothreitol 8.3 mM hemin, 16.6 μg/ml creatine kinase, 0.33 mM calcium chloride, 0.66 mM EGTA, 23.3 mM sodium chloride.

Incubations were carried out at 30° C. for 90 minutes. Dog pancreas microsomal membranes prepared from rough microsomes using EDTA for removal of the ribosomes (Blobel, et al., *J. Cell Biology* 67, 852 (1975)) were treated with nuclease as described (Shields, et al., *J. Biol. Chemistry* 253, 3753 (1978)) and were present in the translation mixture at a final concentration of 7 $A_{260}$ units/ml. Translation products or immunoprecipitated translation products were analyzed by electrophoresis on 10 percent polyacrylamide gels in the sodium dodecyl sulfate as previously described (Laemmli, *Nature* 227, 680 (1970)). The unstained slab gels were fixed, dried and subjected to fluorography (Bonner, et al., *Eur. J. Biochem.* 46, 83 (1974)).

The resulting translation products from each gel fraction were immunoprecipitated with rabbit anti-human plasminogen activator specific IgG. One major immunoprecipitated polypeptide band was observed in the translation of RNA fraction number 7 and 8 (migration of 21 to 24S) having a molecular weight of approximately 63,000 daltons. This band was not observed when preimmune IgG was used for immunoprecipitation which suggested these polypeptides were plasminogen activator specific.

Five μg of gel fractionated mRNA (gel slice 7 mRNA) was used for the preparation of double stranded cDNA by standard procedures (Goeddel, et al., *Nature* 287, 411 (1980), Goeddel, et al., *Nature* 281, 544 (1979), and Wickens, et al., *J. Biol. Chem.* 253, 2483 (1978)). The cDNA was size fractionated on a 6 percent polyacrylamide gel. The cDNA greater than 350 base pairs in length (125 ng) was electroeluted. 30 ng of cDNA was extended with deoxy(C) residues using terminal deoxynucleotidyl transferase (Chang, et al., *Nature* 275, 617 (1978)) and annealed with 300 ng of the plasmid pBR322 (Bolivar, et al., *Gene* 2, 95 (1977)) which had been similarly tailed with deoxy(G) residues at the PST I site (Chang, et al., *Nature* 275, 617 (1978)). The annealed mixture was then transformed into *E. coli* K12 strain 294 (ATCC No. 31446). Approximately 4,600 transformants were obtained.

Purified human plasminogen activator was obtained according to the procedure of disclosed references (European Patent Application Publn. No. 0041766 and Weimar, W., et al., *The Lancet Volume II* 8254, 1018 (1981)).

The molecule was scanned in order to locate regions best suited for making synthetic probes, as follows:

To make the proteins susceptible to digestion by trypsin it was reduced and carboxymethylated. A 2 mg sample of plasminogen activator was first dialyzed against 0.01 percent Tween 80 in water. The lyophilized protein was then dissolved in 2.5 ml of Tris-HCl buffer (pH 8.6) and 8 molar in urea. The disulfide bonds were reduced by additions of 0.1 ml of β-mercaptoethanol. This reaction was carried out under nitrogen for 2 hours. The reduction in sulfides were alkylated to the carboxymethyl derivative by the addition of iodoacetic acid in 1 N NaOH. After 20 minutes the reaction was stopped by dialysis against 0.01 percent Tween 80 in water.

The resulting lyophilized carboxymethylated protein was redissolved in 3 ml of 0.1 M sodium phosphate buffer (pH 7.5). Trypsin (TPCK) was added (1 to 50 ratio) and digested at 37° C. Aliquots (0.1 ml) were taken at 3 hours, 6 hours, and 12 hours. A second addition of trypsin was made after 12 hours. The reaction was stopped after 24 hours by freezing the sample until it could be injected on the HPLC. The progress of the digestion was determined by SDS gels on the aliquots. All gels were blank except for a faint band on the 3 hours aliqout. This indicated that the 24 hour digestion was complete and no large peptides remained.

An analytical amount (ca. 0.5 ml) was injected into a high resolution Altex C-8 ultrasphere 5 μ column with two runs. A gradient of acetonitrile was made gradual (1 percent to 5 percent in 5 min, 5 percent to 35 percent in 100 min, 35–50 percent in 30 min). In one of the two preparative runs, the eluant was monitored at two wavelengths (210 mn and 280 nm). The ratio of the two wavelength absorptions was used to indicate the tryptophan containing peptides.

The peptide peaks most likely to contain tryptophan, or that were believed useful for other reasons, were sequenced first. This enabled that determination of the sequence around most of the tryptophans. After sequencing about 25 of the best possible peptide peaks, all the sequence data that could be aligned was pooled to obtain a preliminary model of the primary structure of plasminogen activator. From this data and model, several possible probes were located.

The colonies were individually inoculated into wells of microliter plates containing LB (Miller, Experiments in Molecular Genetics, p. 431–433 Cold Spring Harbor Lab., Cold Spring Harbor, New York (1972))+5 μl/ml tetracycline and stored at −20° C. after addition of DMSO to 7 percent. Two copies of the colony library were grown up on nitrocellulose filters and the DNA from each colony fixed to the filter by the Grunstein Hogness procedure (Grunstein, et al., *Proc. Natl. Acad. Sci.* (*USA*) 72, 3961 (1975)).

The $^{32}$P-labeled-TC(A,G)CA(A,G)TA(C,T)TCCCA probe was prepared (from the synthetic oligomer) (W-E-Y-C-D) 14-mer pool of 8 radiolabeled synthetic deoxyoligonucleotides (14-mers) TC(AG)CA(AG)TA(CT)TCCCA coding for the known amino acid sequence: tryptophan-glutamic acid-tryosine-cysteine-aspartic acid (W-E-Y-C-D). Filters containing 4,600 transformants were prehybridized for 2 hours at room temperature in 50 mM sodium phosphate pH 6.8, 5X SSC (Blin, et al., *Nucleic Acid Research* 3, 2303 (1976)), 150 μg/ml sonicated salmon sperm DNA, 5X Denhardt's solution (Denhardt, *Biochem. Biophys. Res. Comm.* 23, 641 (1966)) 10 percent formamide and then hybridized with $50\times10^6$ counts per minute of the labelled probe in the same solution. After an overnight incubation at room temperature, the filters were washed 3 times at room temperature in 6X SSC, 0.1 percent SDS for 30 minutes, once in 2X SSC and then exposed to Kodak XR-5 x-ray film with DuPont Lightning Plus intensifying screens for 16 hours.

Plasmid DNA was isolated by a rapid method (Birnboim, et al., *Nucleic Acids Research* 7, 1513 (1979)) from all colonies showing a positive hybridization reaction. The cDNA inserts from these clones were then sequenced after subcloning fragments into the M3 vector mp 7 (Messing, et al., *Nucleic Acids Research* 9, 309 (1981)) and by the Maxam Gilbert chemical procedure (Maxan, et al., *Methods in Enzymol.* 65, 499 (1980)). Filter number 25 showed the hybridization pattern of a positive plasminogen activator clone. The cDNA insert in clone 25E10 was demonstrated to be the DNA coding for plasminogen activator by comparing its amino acid sequence with peptide sequence obtained from purified plasminogen activator and by its expression product produced in *E. coli* as described in more detail infra. Clone 25E10 was 2304 base pairs in length with the longest open reading frame encoding protein of 508 amino acids (MW of 56,756) and containing a 772 bp 3' untranslated region. This cDNA clone lacked the N-terminal coding sequences.

50 μg of pPA25E10 (supra) were digested with Pst I and the 376 bp fragment isolated by electrophoresis on a 6 percent polyacrylamide gel. Approximately 3 μg of this fragment was isolated from the gel by electroeluting, digested with 30 units of Dde I for 1 hour at 37° C. phenol and chloroform extracted, and ethanol precipitated. The resulting Dde I sticky ends were extended to blunt ends by adding 5 units of DNA polymerase I (Klenow fragment) and 0.1 mM each of dATP, dCTP, dGTP, dTTP to the reaction mixture and incubating at 4° C. for 8 hours. After extraction with phenol and chloroform, the DNA was digested with 15 units of Nar I for 2 hours and the reaction mixture electrophoresed on a 6 percent polyacrylamide gel. Approximately 0.5 μg of the desired 125 bp blunt end Nar I fragment was recovered. This fragment codes for amino acids number 69 through 110 of the mature full length plasminogen activator protein.

For isolation of the 1645 bp Nar I - Bgl II fragment, 30 μg of pPA25E10 were digested with 30 units of Nar I and 35 units of Bgl II for 2 hours at 37° C. and the reaction mixture electrophoresed on a 6 percent polyacrylamide gel. Approximately 6 μg of the desired 1645 bp Nar I - Bgl II fragment were recovered.

The plasmid pΔR1SRC is a derivative of the plasmid pSRCex16 (McGrath and Levinson, *Nature* 295, 423 (1982)) in which the Eco RI sites proximal to the trp promoter and distal to the SRC gene have been removed by repair with DNA polymerase I (Itakura, et al., *Science* 198, 1056 (1977)), and the self-complementary oligodeoxynucleotide AATTATGAATTCAT (synthesized by the phosphotriester method (Crea, et al., *Proc. Natl. Acad. Sci.* (*USA*) 75, 5765 (1978)) was inserted into the remaining Eco RI site immediately adjacent to the Xba I site. 20 μg of pΔR1SRC were digested to completion with Eco RI, phenol and chloroform extracted, and ethanol precipitated. The plasmid was then digested with 100 units of nuclease S1 at 16° C. for 30 minutes in 25 mM sodium acetate (pH 4.6), 1 mM $ZnCl_2$ and 0.3 M NaCl to create a blunt end with the sequence ATG. After phenol and chloroform extraction and ethanol precipitation, the DNA was digested with Bam HI, electrophoresed on a 6 percent polyacrylamide gel, and the large (4,300 bp) vector fragment recovered by electroelution.

The expression plasmid was assembled by ligating together 0.2 μg of vector, 0.06 μg of the 125 bp blunt end - Nar I fragment and 0.6 μg of the 1645 bp Nar I - Bgl II fragment with 10 units of T4 DNA ligase for 7 hours at room temperature and used to transform *E. coli* strain 294 (ATCC No. 31446) to ampicillin resistance. Plasmid DNA was prepared from 26 of the colonies and digested with Xba I and Eco RI. Twelve of these plasmids contained the desired 415 bp Xba I - Eco RI and 472 bp Eco RI fragments. DNA sequence analysis verified that several of these plasmids had an ATG initiation codon correctly placed at the start of amino acid number 69 (serine). One of these plasmids, pΔRIPA° was tested and produced the desired plasminogen activator.

0.4 μg of the synthetic oligonucleotide 5' TTCTGAGCACAGGGCG 3' was used for priming 7.5 μg of gel fraction number 8 (supra) to prepared double stranded cDNA by standard procedures (Goeddel, et al., *Nature* 281, 544 (1979), and Wickens, et al., *J. Biol. Chem* 253, 2483 (1978)). The cDNA was size fractionated on a 6 percent polyacrylamide gel. A size fraction greater than 300 base pairs (36 ng) was electroeluted. 5 ng cDNA was extended with deoxy(C) residues using terminal deoxycytidyl transferase (Chang, et al., *Nature* 275, 617 (1978)) and annealed with 50 ng of the plasmid pBR322 (Bolivar, et al., *Gene* 2, 95 (1977)) which had been similarly tailed with deoxy(G) residues at the Pst I site (Chang, et al., supra). The annealed mixture was then transformed into *E. coli* K12 strain 294. Approximately 1,500 transformants were obtained.

Since the cDNA priming reaction had been done using a synthetic fragment that hybridized 13 base pairs from the N-terminal of clone 25E10, no convenient restriction fragment was available in this 29 base pair region (which includes the 16-mer sequence) for screening the cDNA clones. Therefore, it was necessary to isolate a human plasminogen activator genomic clone in order to identify any primer extended cDNA clones containing N-terminal plasminogen activator coding sequences.

The first step in this process involved establishing the fact that only a single homologous plasminogen activator gene is present in human genomic DNA. To determine this, a Southern hybridization was performed. In this procedure (Southern, *J. Mol. Biol.* 98, 503 (1975)), 5 μg of high molecular weight human lymphocyte DNA (prepared as in Blin, et al., *Nucleic Acid Research* 3, 2303 (1976)) was digested to completion with various restriction endonucleases, electrophoresed on 1.0 percent agarose gels (Lawn, et al., *Science* 212, 1159 (1981)) and blotted to a nitrocellulose filter (Southern, supra). A $^{32}$P-labelled DNA probe was prepared (Lawn, et al., *Cell* 15, 1157 (1978)) from the 5' end of the cDNA insert of the cDNA clone 25E10 (a 230 bp HPA II - Rsa I fragment) and hybridized (Fritsch, et al., *Cell* 19, 959 (1980) with the nitrocellulose filter. $35\times10^6$ counts per minute of the probe were hybridized for 40 hours and then washed as described (Fritsch, et al. supra). Two endonuclease digestion patterns provide only a single hybridizing DNA fragment: Bgl II (5.7 Kbp) and Pvu II (4.2 Kbp). Two hybridizing DNA fragments were observed with Hind II (5.1 Kbp and 4.3 Kbp). Taken together, these data suggest the presence of only a single plasminogen activator gene in the human genome, and that this gene contains at least one intervening sequence.

The strategy used to identify λ phase recombinants carrying plasminogen activator genes consisted in detecting nucleotide homology with a radioactive probe prepared from the plasminogen activator clone p25E10. One million recombinant λ phage were plated out on DP 50 Sup F at a density of 10,000 pfu/15 cm plate, and nitrocellulose filter replicas were prepared for each plate by the method of Benton and Davis (Benton, et al., *Science* 196, 180 (1977)). A $^{32}$P-labelled DNA probe was prepared by standard procedures (Taylor, et al., *Biochem. Biophys. Acta* 442, 324 (1976)) from a 230 base pair Hpa II - Rsa I fragment located 34 base pairs from the 5' end of the clone p25E10. Each nitrocellulose filter was prehybridized at 42° C. for 2 hours in 50 mM sodium phosphate (pH 6.5), 5X SSC (Southern, supra), 0.05 mg/ml sonicated salmon sperm DNA, 5X Denhardt's solution (Denhardt, supra), 50 percent formamide and then hybridized with $50\times10^6$ counts per minute of the labelled probe in the same solution containing 10 percent sodium dextran sulfate (Wahl, et al., *Proc. Natl. Acad. Sci.* (*USA*) 76, 3683 (1979)). After an overnight incubation at 42° C., the filters were washed 4 times at 50° C. in 0.2X SSC, 0.1 percent SDS for 30 minutes, once in a 2X SSC at room temperature and then exposed to Kodak XR-5 x-ray film with Dupont Cronex intensifying screens overnight. A total of 19 clones were obtained which hybridized with the probe. Phage DNA was prepared as previously described (Davis, et al., Advanced Bacterial Genetics, Cold Spring Harbor Laboratory, New York (1980)) from 6 recombinants. λ Clone C was selected for preparation of a Pvu II fragment colony screening. 30 μg of DNA was digested with Pvu II for 1 hour at 37° C., and electrophoresed on 1.0 percent agarose gels. A 4.2 Kilobase pair fragment previously shown to contain plasminogen activator sequences was electroeluted and purified. A $^{32}$P-labelled probe was prepared by standard procedure (Taylor, et al., supra) for colony hybridizations as described infra.

The colonies were transferred from plates and grown on nitrocellulose filters and the DNA from each colony fixed to the filter by the Grunstein - Hogness procedure (Grunstein, et al., supra). A $^{32}$P-labelled probe was made by calf-thymus priming (Taylor, et al., supra) a 4.2 kilobase pair Pvu II fragment from an isolate plasminogen activator λ genomic clone. Filters containing the 1,500 transformants were hybridized with $112\times10^6$ cpm of $^{32}$P-genomic Pvu II fragment. Hybridization was for 16 hours using conditions described by Fritsch, et al. (supra). Filters were extensively washed and then exposed to Kodak XR-5 x-ray film with Dupont Lightning Plus intensifying screens for 16–48 hours. Eighteen colonies clearly hybridized with the genomic probe. Plasmid DNA was isolated from each of these colonies and was bound to nitrocellulose filters and hybridized with the $^{32}$P-labelled synthetic oligonucleotide (16-mer) used for the original priming reaction. Of the 18 clones, seven hybridized with the kinased 16-mer. Upon sequence analysis after subcloning fragments into the L3 vector $mp^7$ (Messing, et al., supra), one clone (pPA17) was shown to contain the correct 5' N-terminal region of plasminogen activator, a signal leader sequence and an 84 bp 5' untranslated region. From the two clones pPA25E10 and pPA17 the complete nucleotide sequence and restriction pattern of a full length plasminogen activator clone were determined.

A reconstruction of the entire coding sequence was possible employing common Hha I restriction endonuclease site shared by both patrial clones PA17 and 25E10. A 55 bp Sau3AI-HhaI restriction fragment corresponding to amino acids 5–23 was isolated from the plasmid pPA17. The Sau3AI restriction site was located at codon four of the presumed mature coding sequence and was used to remove the signal peptide coding region. A 263 bp HhaI-NarI fragment (coding for amino acids 24–110) was also isolated from plasmid p25E10. Two synthetic deoxyoligonucleotides were designed which restore the codons for amino acids 1–4, incorporate an ATG translational initiation codon and create an EcoRI cohesive terminus. These three fragments were then ligated together to form a 338 bp fragment coding for amino acids 1–110. This fragment and a 1645 bp NarI-BglII fragment from p25E10 were then ligated between the EcoRI and BglII sites of the plasmid pLelFAtrp103 (Gray, et al., *Nature* 295, 503 (1982)) to give the expression plasmid pEPAtrp12. The cloned EPA gene is transcribed under the control of a 300 bp fragment of the *E. coli* trp operon which contains the trp promoter, operator, and the Shine-Dalgarno sequence of trp leader peptide but lacks the leader peptide ATG initiation codon (Goeddel, et al., *Nature* 287, 411 (1980)). Three fragments from overlapping tPA plasmids, pPa25E10 (ATCC 40401) and pPA17 (ATCC 40402 and pt-PAtrp12 (ATCC 40404) were prepared as follows: Plasmid pPa17 was digested with Dde I, filled in using Klenow DNA polymerase I, and subcut with Pst I; the approximately 200 bp fragment containing 5' terminal tPA sequence thus generated was isolated. The second tPA fragment was obtained by digesting pt PAtrp12 with Pst I and Nar I and isolating the approximately 310 bp fragment. The third tPA fragment was obtained by digesting pPA25E10 with Nar I and Bgl II and isolating the approximately 1645 bp fragment which contains, in addition to much of the tPA coding region, some 3' non-translated sequences. Bacterial clones *E. coli* (pPA25E10), *E. coli* (pPA17) and *E. coli* (pΔRIPA°) have been deposited with the American Type Culture Collection and accorded accession numbers 67587, 67586 and 67585, respectively.

Plasmid p342E which expresses HBV surface antigen (also referred to as pHBs348-E) has been described by Levinson et al, patent application Ser. No. 326,980, filed Dec. 3, 1981, which is incorporated herein by reference. The origin of SV40 was isolated by digesting SV40 DNA with Hind III, and converting the Hind III ends to EcoRI ends by the addition of a converter (AGCTGAATTC). This DNA cut with PvuIII, and RI linkers added. Following digestion with EcoRI, the 348 base pair fragment spanning the origin was isolated by polyacrylamide gel electrophoresis and electroelution, and cloned in pBR322. Expression plasmids pHBs348-E and pHBs348-L were constructed by cloning the 1986 base-pair fragment resulting form EcoRI and BglII digestion of HBV (*Animal Virus Genetics* (Ed. Fields, Jaenisch and Fox), Chapter 5, p. 57, Academic Press, New York (1980)) (which spans the gene encoding HBsAg) into the plasmid pML (Lusky and Botchan, *Nature* 293, 79 (1981)) at the EcoRI and BamHI sites. (pML is a derivative of pBR332 which has a deletion eliminating sequences which are inhibitory to plasmid replication in monkey cells (Lusky and Botchan, supra.)) The resulting plasmid (pRI-Bgl) was then linearized with EcoRI, and the 348 base-pair fragment representing the SV40 origin region was introduced into the EcoRI site of the pRI-Bgl. The origin fragment can insert in either orientation. Since this fragment encodes both the early and late SV40 promoters in addition to the origin of replication, HBV genes could be expressed under the control of either promoter depending on this orientation (pHBS348-E representing HBs under control of the early promoter). pE342 is modified by digesting with trace amounts of Eco RI, filling in the cleaved site using Klenow DNA polymerase I, and ligating the plasmid back together, thus removing the Eco RI site preceding the SV40 origin in pE342. The resulting plasmid, designated pE342ΔRI, is digested with Eco RI, filled in using Klenow DNA polymerase I, and subcut with Bam HI. After electrophoresing on acrylamide gel, the approximately 3500 bp fragment is electroeluted, phenol-chloroformed, and ethanoled as above.

The thus prepared p342E 3500 bp vector, and above described tPA fragments comprising approximately 2160 bp were ligated together using standard techniques. A plasmid containing the three tPA encoding fragments in the proper orientation was isolated, characterized, and designated pE342-tPA. This plasmid was digested with Sac II and treated with bacterial alkaline phosphatase (BRL). To provide the DHFR sequence (along with control sequences for its expression) an approximately 1700 bp fragment was generated by SacII digestion of pEHER. (pEHER is a plasmid expressing mutant DHFR described in copending U.S. Ser. No. 06/459,151.) This fragment was ligated into the pE342-tPA plasmid to create pETPAER400, a plasmid which is analagous to pEHER except that the HBsAg coding region has been replaced by the cDNA sequences from tPA, C.1.B Expression and Amplification of the tPA Sequence pETPAER400 (pETPER) was transfected into both $dhfr^-$ (CHO-DOX 811) obtained by permission from Urlaub and Chasin, and $DHFR^+$OCHO-K1 (ATCC CCL61) cells by the method of Graham and Van der Eb (supra). Transformed $dhfr^-$ cells were selected by growth in glycine, hypoxanthine and thymidine deficient medium. Transformed $DHFR^+$ cells were selected by growth in > 100 nM MTx. Colonies which arose on the appropriate selection medium were isolated using cloning rings and propagated in the same medium to several generations.

For amplification cells from the colonies are split into media containing $5\times10^4$, $10^5$, $2.5\times10^5$, $5\times10^5$, and $10^6$ nM MTx and passaged several times. Cells are plated at very low ($10^2$–$10^3$ cells/plate) cell densities in 10 cm dishes and the resulting colonies are isolated as usual.

C.1.C Assay Methods

Expression of tPA in the transfected amplified colonies may conveniently be assayed by the methods set forth in U.S. application Ser. No. 398,003. Briefly, for quantitative assay, the medium or extract to be tested is placed in a solution containing plasminogen, and the amount of plasmin formed is measured by monitoring the cleavage of a chromogenic substrate such as S2251, Kabi Group Inc., Greenwich, Conn. An aliquot of the sample is mixed with 0.1 ml of 0.7 mg/ml plasminogen (in 0.5M Tris-HCl, pH 7.4, containing 0.012M NaCl) and the volume adjusted to 0.15 ml. The mixture is incubated at 37° C. for ten minutes, 0.35 ml of S2251 (1.0 mM solution in the above buffer) is added and the reaction continued for 30 minutes at 37° C. Acetic acid (25 μl) is added to terminate the reaction. The samples are centrifuged and the absorbance at 405 nm is measured.

Quantitation of the amount of activity is obtained by comparison with a standard urokinase solution. The assay conditions for detection of a full length plasminogen activator were modified by the addition of fibrinogen (0.2 mg) to the solution. Fibrinogen results in a stimulation of the activity of plasminogen activator observed, therefore resulting in somewhat elevated levels of activity. Activity was recorded in Plough units, wherein 90,000 Plough units is equal to the activity exhibited by 1 mg of purified tissue plasminogen activator.

Coamplification of DHFR and tPA sequences is assayed by isolating DNA from confluent monolayers of amplified colonies as follows: Confluent monolayers in 150 mm plates are washed with 50 ml sterile PBS and lysed by the addition of 5 ml of 0.1 percent SDS, 0.4 M $CaCl_2$, 0.1 M EDTA, pH 8. After 5–10 minutes, the mixture is removed, phenol extracted, chloroform extracted, and ethanol precipitated. The DNA is resuspended in 1 ml (per 150 mm plate) 10 mM Tris pH 8, 1 mM EDTA (TE), RMase added to 0.1 mg/ml, and the solution incubated 30 minutes at 37°. SDS is then added to 0.1 percent and pronase (Sigma) is added to 0.5 mg/ml. After 3–16 hours incubation at 37°, the solution is again phenol extracted, chloroform extracted, and ethanol precipitated as usual. The DNA pellet is resuspended in 0.5 ml water and digested with restriction enzymes as per the standard protocol. Approximately 5–10 μg of digested DNA is electrophoresed in an agarose gel [1 percent agarose in Tris - acetate bufffer (40 mM Tris, 1 mM EDTA, made to pH 8.2 with acetic acid)]; Crouse, et al, *J. Biol. Chem.,* 257: 7887 (1982)). After bromphenol blue dye had migrated ⅔ of the way down the gel, the gel is removed and stained with ethidium bromide. After visualizing the DNA with ultraviolet light, the gel is treated with HCl, NaOH, and NaCl-Tris and transferred to nitrocellulose filters according to the procedure of Southern (*J. Mol. Biol.* 98: 503. (1975)). The filters are then hybridized with a nick translated probe made from the 1700 bp SacII fragment of pEHER (prepared and hybridized as described above), or from the approximately 1970 bp Bgl II fragment of pETPER.

C.2 Production of tPA in Conjunction With Wild Type DHFR Protein

C.2.A Vector Construction

In a manner exactly analogous to that used in the construction of pETPER, a plasmid containing the DNA sequence encoding wild type DHFR, pETPFR (ATCC 40403), was constructed. The construction was exactly as described in Example C.1.A except that in place of plasmid pEHER as a source for the DHFR protein gene sequence, the plasmid pE342.HBV.E400.022 described in copending U.S. Ser. No. 06/454,152 was substituted. pE342 is modified by partially digesting with EcoRI, filling in the cleaved site using Klenow DNA polymerase I, and ligating the plasmid back together, thus removing the EcoRI site preceding the SV40 origin in pE342. The resulting plasmid, designated pE342ΔR1, is digested with EcoRI, filled in using Klenow DNA polymerase I, and subcut with BamHI. After electrophoresing on acrylamide gel, the approximately 3500 bp fragment is electroeluted, phenol-chloroform extracted, and ethanol precipitated as above. The 5' nontranslated leader region of HBsAg was removed by treatment with EcoRI and with Xba, and the analogous 150 bp EcoRI-Xba fragment of a hepatitis expression plasmid pHS94 (Liu, et al., *DNA* 1, 213 (1982)) was inserted in its place to create pE342.HS94.HBV.

The 1600 bp PstI insert of the DHFR cDNA plasmid DHFR-11 (Nunberg, et al., *Cell* 19, 355 (1980)) was treated with the exonuclease Bal31 in order to remove the poly G:C region adjacent to the Pst I sites, digested with BglII and the resulting fragments of approximately 660 bp isolated from gels. The Bal31-BglII digested cDNA was ligated into a pBR322 plasmid derivative containing a BglII site. (Following digestion of pBR322 with Hind III, the plasmid fragment was filled in using Klenow DNA polymerase in the presence of the four deoxynucleotide triphosphates, and subcut with BglII.) The resulting plasmid, pDHFR-D22, has an EcoRI site situated 29 bp upstream of the fusion site between pBR322 and the 5' end of the DHFR cDNA. The EcoRI-BglII fragment encompassing the coding sequences of the cDNA insert was then excised from pDHFR-D22 and ligated to EcoRI-BamHI digested pE342.HS94.HBV, creating the DHFR expression plasmid pE342.D22. pE342.HBV.D22 was constructed by ligating the EcoRI-TaqI fragment of cloned HBV DNA (Liu, et al., supra), to EcoRI-ClaI digested pE342.D22. This plasmid was further modified by fusing an additional SV40 early promoter between the BglII site and the ClaI site of the DHFR insert of pE342.HBV.D22, creating pE342.HBV.E400.D22. The plasmid pE342.HBV.E400.D22 is exactly the same as pEHER except for a single base pair difference between wild type and mutant DHFR. Thus the resulting plasmid pETPFR is analogous in every way to pETPER except that the DNA sequence encoding for wild type DHFR is substituted for that of the mutant.

C.2.B Expression of tPA Sequence pETPFR was used to transfect DHFR deficient CHO cells (Urlaub and Chasin (supra)) using the calcium phosphate precipitation method of Graham and Van der Eg. Twenty-one colonies which arose on the selective medium (−HGT) were assayed by detection of plasmin formation as assessed by the digestion of fibrin in an agar plate containing fibrin and plasminogen, described by Granelli-Piperno, et al, *J. Exp. Med.,* 148: 223 (1978).

Four of the best positive clones were then assayed quantitatively for plasmin formation on a per cell basis according to the method set forth in C.1.C.

Upon each quantitative determination it was found that the four clones tested exhibited the same or comparable tPA secretion into the medium, determined as units/cell/day. Subclones were prepared by transferring inocula from two of the clones into separate plates containing −HGT medium. Two of the resulting subclones, IdB and I were used for further analysis.

C.2.C Amplification and tPA Production Levels

The above subclones were plated at $2\times10^5$ cells per 100 mm plates in 50 nM MTX to promote amplification. Those cells which survived, when assayed as described above, gave, in all cases, about 10 times the unamplified amount of plasminogen activator activity. Two of these clones were chosen for further study and were named 1-15 and 188-9.

Subclone 1-15 was further amplified by seeding $2\times10^5$ cells in 100 mm plates containing 500 nM MTX. Assay of the cells thus amplified yielded a further increase (of about 3 fold) in tPA production; when assayed quantitively by the method of C.1.C. levels were in the range of $7\times10^{-4}$ units/cell/day. A portion of these amplified cells was then transferred and maintained in the presence of 10,000 nM MTX. Subclones of 1-15, and 188-9 were further tested after being maintained for approximately 1–2 months at the conditions specified in Table 1.

TABLE 1

| Cell Line | Growth Conditions | ng tPA/cell/day* |
|---|---|---|
| $1\text{-}15_{500}$ | 500 nM MT X | $28.5 \times 10^{-3}$ |
| $1\text{-}15_{500}$ | 500 nM MT X | $26.0 \times 10^{-3}$ |
| $1\text{-}15_{500}$ | (−MGT medium, no MT X) | $8.3 \times 10^{-3}$ |
| $1\text{-}15_{500}$ | (−MGT medium, no MT X) | $18.0 \times 10^{-3}$ |
| $1\text{-}15_{10,000}$ | 10 uM MT X | $29.3 \times 10^{-3}$ |
| $1\text{-}15_{10,000}$ | 10 uM MT X | $49.0 \times 10^{-3}$ |
| 188-9 | 50 uM MT X | $14.3 \times 10^{-3}$ |
| 188-9 | 50 uM MT X | $14.4 \times 10^{-3}$ |
| 188-9 | (−MGT medium, no MT X) | $14.3 \times 10^{-3}$ |
| 188-9 | (−MGT medium, no MT X) | $14.4 \times 10^{-3}$ |
| 1 | (−MGT medium, no MT X) | $1.0 \times 10^{-3}$ |
| 1 | (−MGT medium, no MT X) | $0.7 \times 10^{-3}$ |

*tPA in the culture medium was assayed quantitatively in a radioimmuno assay as follows: Purified tPA and purified lodinated tracer tPA derived from melanoma cells were diluted serially to include concentration of 12.5 to 400 ng/ml in a buffer containing phosphate buffered saline, pH 7.3, 0.5 percent bovine serum albumin, 0.01 percent Tween 80, and 0.02 percent NaN3. Appropriate dilutions of medium samples to be assayed were added to the radioactively labelled tracer proteins. The antigens were allowed to incubate overnight at room temperature in the presence of a 1:10,000 dilution of the IgG fraction of a rabbit anti-tPA antiserum. Antibody-antigen complex was precipitated by absorption to goat anti-rabbitIgG Immunobeads (BioRad) for two hours at room temperature. The beads were cleared by the addition of saline diluent followed by centrifugation for ten minutes at 2000 × g at 4° Celsius. Supernatants were discarded and the radioactivity in the precipitates was monitered. Concentrations were assigned by comparison with the reference standard.

The cell lines are as follows: Cell line "1" is an unamplified clone from the original set of four. "$1\text{-}15_{500}$" is an amplified subclone of cell line "1" which was amplified initially in 50 nM MTX to give 1-15 and then transferred for further amplification into 500 nM MTX. $1\text{-}15_{10,000}$ is subclone of $1\text{-}15_{500}$ which has been further amplified in the presence of 10,000 nM MTX. Cell line 188-9 is a subclone of one of the original four detected which had been amplified on 50 nM MTX. The CHO cell line CHO $1\text{-}15_{500}$ has been deposited with the American Type Culture Collection and accorded accession number CRL 9606.

All of the amplified cells show increased levels of TPA production over that exhibited by the unamplified cell culture. Even the unamplified culture produces amounts of tPA greater than 0.5 pg/cell/day; amplification results in levels approaching 50 pg/cell/day.

What is claimed is:

1. A method of producing human tissue plasminogen activator, which comprises cultivating a human tissue plasminogen activator-producing recombinant Chinese hamster ovary cell line in a nutrient culture medium which is substantially free of serum and which is substantially free of plasmin and plasminogen.

2. A method of producing human tissue plasminogen activator, which comprises cultivating a DHFR deficient Chinese hamster ovary cell line containing DNA operatively encoding DHFR and human tissue plasminogen activator in a nutrient culture medium which is substantially free of serum and which is substantially free of plasmin and plasminogen.

* * * * *